(12) United States Patent
Marsh

(10) Patent No.: US 6,520,961 B1
(45) Date of Patent: Feb. 18, 2003

(54) METHOD AND APPARATUS FOR EXTERNAL FIXATION OF A HINGED JOINT

(75) Inventor: J. Lawrence Marsh, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 169 days.

(21) Appl. No.: 09/724,264

(22) Filed: Nov. 28, 2000

Related U.S. Application Data

(63) Continuation-in-part of application No. 09/034,669, filed on Mar. 4, 1998, now Pat. No. 6,152,925.

(51) Int. Cl.⁷ .............................................. A61B 17/56
(52) U.S. Cl. .......................................... 606/54; 606/56
(58) Field of Search ................................ 606/53–59, 73

(56) References Cited

U.S. PATENT DOCUMENTS 5,376,091 A * 12/1994 Hotchkiss et al. ............. 602/22
5,931,837 A * 8/1999 Marsh et al. .................. 606/54

\* cited by examiner

Primary Examiner—Roy D. Gibson
(74) Attorney, Agent, or Firm—Harness, Dickey & Pierce, P.L.C.

(57) ABSTRACT

An apparatus for aligning a mechanical pivot axis of an external fixator with an anatomical pivot axis of a hinged joint. The hinged joint has first and second bones on opposite sides of the anatomical pivot axis. The external fixator has a central body connecting a first bone screw clamping assembly and a second bone screw clamping assembly. The central body includes the mechanical pivot axis. The apparatus for aligning includes an alignment member and a connecting member. The alignment member has a longitudinal axis for alignment with the anatomical pivot axis. The connecting member has a first end adjustably secured to the alignment member and a second end adjustably secured to the first bone screw clamping assembly.

20 Claims, 8 Drawing Sheets

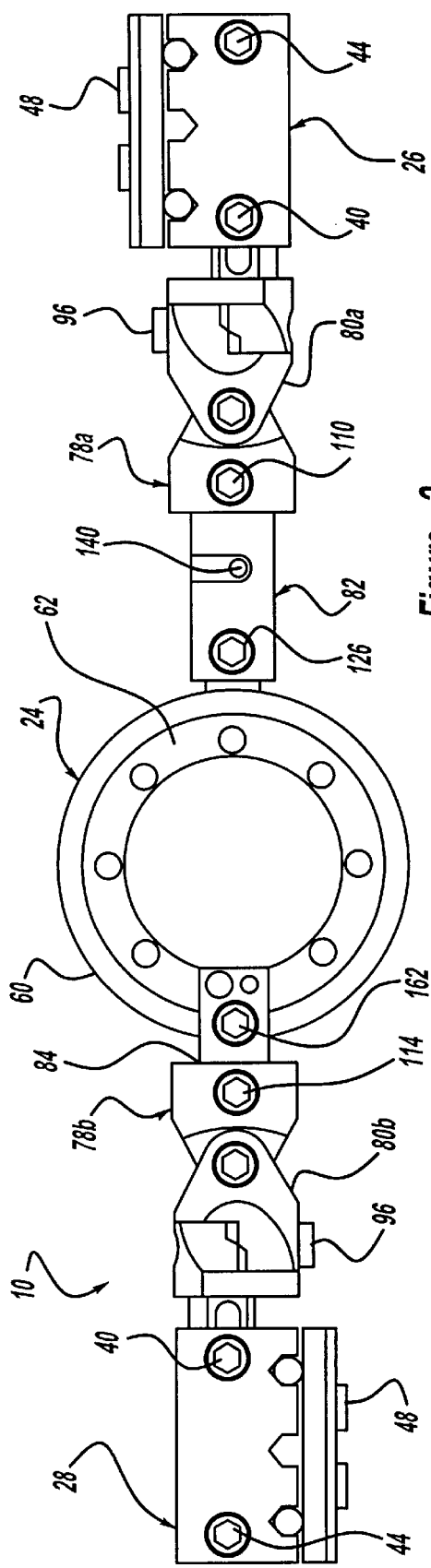
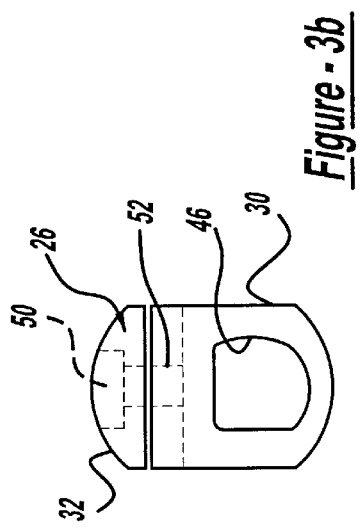
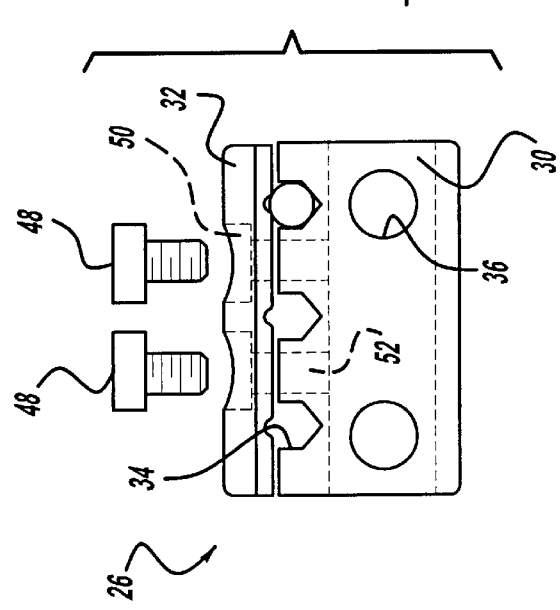

METHOD AND APPARATUS FOR EXTERNAL FIXATION OF A HINGED JOINT

This is a continuation-in-part of U.S. patent application Ser. No. 09/034,669, filed Mar. 4, 1998, now U.S. Pat. No. 6,152,925, issued Nov. 28, 2000.

BACKGROUND OF THE INVENTION

1. Field of the Invention

The present invention relates to an external fixator for use in orthopedic surgical applications, and more particularly to a method and apparatus for external fixation of a hinged joint.

2. Discussion of the Related Art

In various orthopedic surgical procedures, it is necessary to secure two bone portions in a relatively fixed relationship to each other. For example, the need for establishing such a secured relationship is often a result of a fracture which has occurred to the bone. To ensure that the bone can regenerate in the proper orientation and fuse the fracture, it is important that the bone portions be fixed and in the desired position during bone regeneration.

Various external fixation devices for the repair of traumatized bone are known. For example, U.S. Pat. No. 5,662,650 to Bailey et al. discloses an apparatus for the external fixation of large bones. The apparatus is illustrated to include a main body as well as a first and second bone screw clamps. The main body serves to allow the apparatus to axially rotate, thereby providing a proper longitudinal rotational location of the bone screws with respect to a bone. The first bone screw clamp is used to secure a first bone screw to the apparatus while permitting the first bone screw to be axially displaced from the main body. In a similar fashion, the second bone screw clamp functions to secure a second bone screw to the apparatus and to allow the second bone screw to be axially displaced with respect to the main body. U.S. Pat. No. 5,662,650 is incorporated by reference as if fully set forth herein.

In certain orthopedic surgical procedures, it is necessary to employ an external fixation device for immobilizing or restricting motion of a hinged joint such as the elbow joint. Many known devices for externally fixating an elbow joint require the insertion of an axis pin through the anatomical pivot axis. Another known device for elbow fixation is disclosed in U.S. Pat. No 5,100,403 to Hotchkiss et al. which is entitled "Dynamic Elbow Support." The dynamic elbow support has proximal and distal support sections, means for rigidly connecting each support section to bone, and a pair of hinges connecting the support sections and pivoting at the joint. The pair of hinges permits movement of the support sections and their corresponding attached bone throughout flexion and extension. The hinge may be driven by a gear mechanism which may be disengaged by a clutch. The dynamic elbow support may also include a distraction mechanism for movement of the bones out of contact in the joint, while allowing for an active range of motion at the joint.

While known external fixators specifically designed for supporting a hinged joint may have proven to be acceptable for certain applications, such fixators and their application are nevertheless susceptible to improvements that may enhance their performance. In this regard, it is important that a mechanical pivot axis of an external fixator be aligned with the anatomical pivot axis of the hinged joint.

SUMMARY OF THE PRESENT INVENTION

According to one aspect, the present invention generally relates to an apparatus for aligning a mechanical pivot axis of an external fixator with an anatomical pivot axis of a hinged joint. The hinged joint has first and second bones on opposite sides of the anatomical pivot axis. The external fixator has a central body connecting a first bone screw clamping assembly and a second bone screw clamping assembly. The central body includes the mechanical pivot axis. The apparatus for aligning includes an alignment member and a connecting member. The alignment member has a longitudinal axis for alignment with the anatomical pivot axis. The connecting member is adjustably secured to the alignment member and adjustably secured to the first bone screw clamping assembly.

According to another aspect, the present invention relates to a method of aligning a mechanical pivot axis of an external fixator with an anatomical pivot axis of a hinged joint. The hinged joint has first and second bones on opposite sides of the anatomical pivot axis. The method includes the steps of providing an external fixator having first and second bone screw clamping assemblies connected by a central body, the central body having a mechanical pivot axis. The method additionally includes the steps of securing the first bone screw clamp assembly to the first bone through at least one bone screw and aligning an longitudinal axis of an alignment member with the anatomical axis. The method further includes the steps of interconnecting the alignment member with the first bone screw clamp assembly and aligning the longitudinal axis of the alignment member with the mechanical pivot axis.

An advantage of the present invention is the provision of a method and apparatus for external elbow fixation which allows for optimal alignment through hinge positioning which is independent from bone pin placement.

A related advantage of the present invention is the provision of a method and apparatus for external fixation which affords flexible pin placement to avoid damage to local neurovascular structures and ligaments.

Another advantage of the present invention is the provision of a method and apparatus for external elbow fixation which permits movement of a hinge assembly relative to bone pins engaged with the humerus and ulna.

Another advantage of the present invention is the provision of a method and apparatus for external elbow fixation which allows complete radiographic access of the elbow joint from the lateral view to determine "best fit" hinge axis.

Another advantage of the present invention is the provision of a method and apparatus for external elbow fixation which facilitates elbow joint distraction.

Another advantage of the present invention is the provision of a method and apparatus for external fixation of an elbow joint eliminates the requirement for an elbow axis pin.

Another advantage of the present invention is the provision of a method and apparatus for precise alignment of a mechanical pivot axis of an external fixator with the anatomical pivot axis of a hinged joint.

Additional advantages and features of the present invention will become apparent from the following description and appended claims, taken in conjunction with the accompanying drawings.

BRIEF DESCRIPTION OF THE DRAWINGS

FIG. 2 is an enlarged view of the apparatus for external fixation of an elbow joint according to the teachings of the preferred embodiment of the present invention.

FIGS. 3A and B are illustrations showing the central body of the bone screw clamping assembly shown in FIG. 2 according to the teaching of the preferred embodiment of the present invention.

DETAILED DESCRIPTION OF THE PREFERRED EMBODIMENT

The following description of the preferred embodiment of the present invention is merely exemplary in nature and is in no way intended to limit the invention or its application or uses.

Figure 1A:
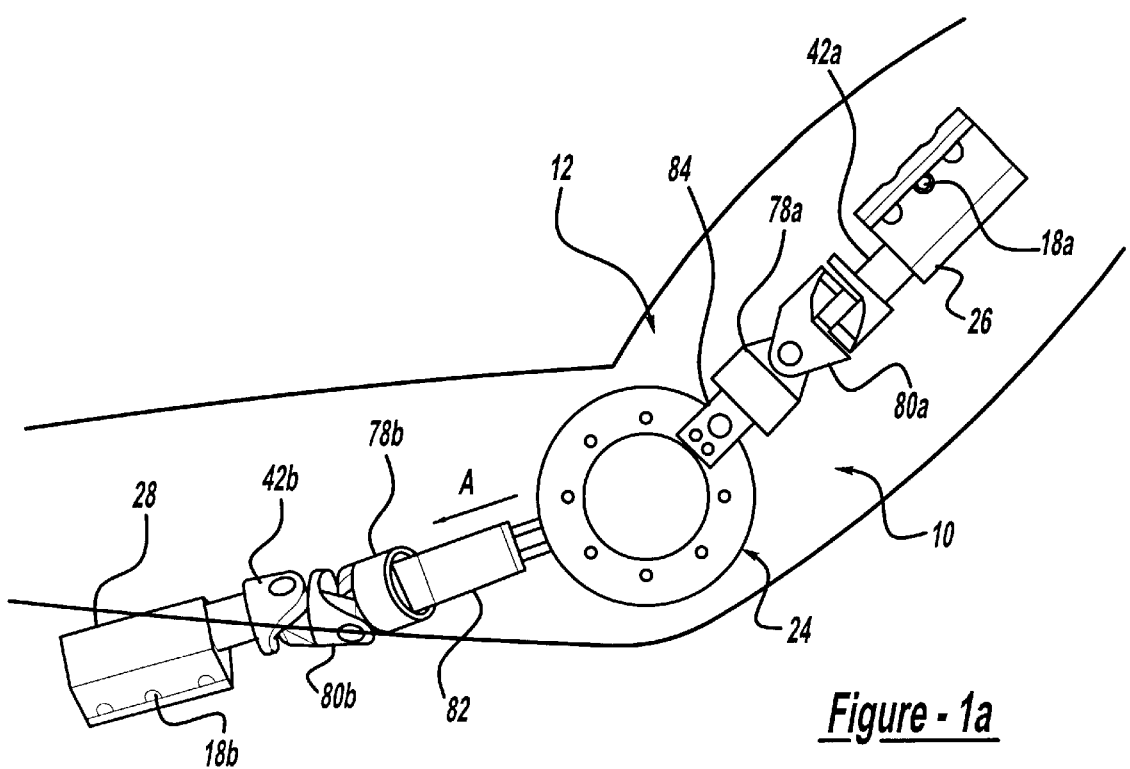
FIGS. 1A and 1B are views of the apparatus for external fixation of an elbow joint according to the teachings of the preferred embodiment of the present invention shown in operative association with a human elbow joint.
Figure 1B:
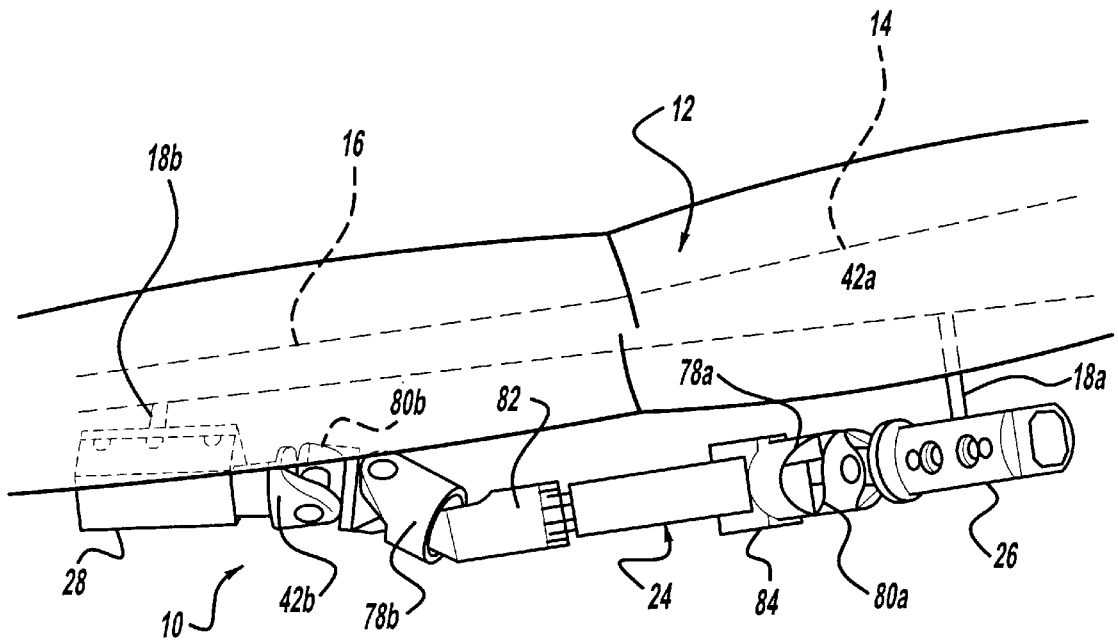
Figure 4A:
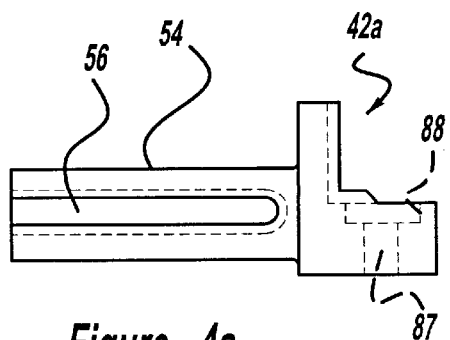
FIGS. 4A, 4B and 4C are illustrations of a rail member shown in FIG. 2 according to the teachings of the preferred embodiment of the present invention.
Figure 4B:
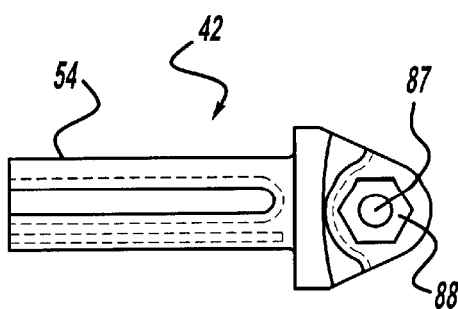
Figure 4C:
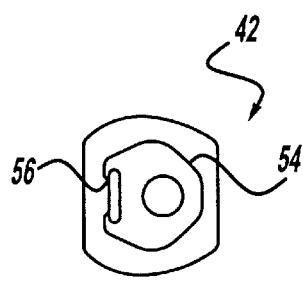
Figure 7A:
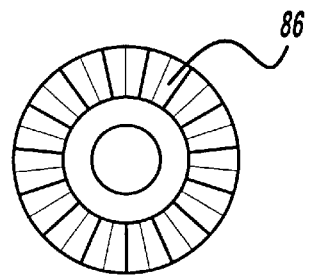
FIGS. 7A and 7B are illustrations showing one of the grooved locking washers shown in FIG. 2 according to the teachings of the preferred embodiment of the present invention.
Figure 5:
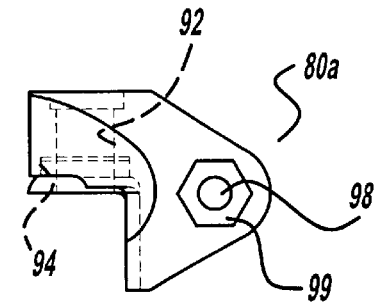
FIG. 5 is an illustration of a connector member shown in FIG. 2 according to the teachings of the preferred embodiment of the present invention.
Figure 7B:
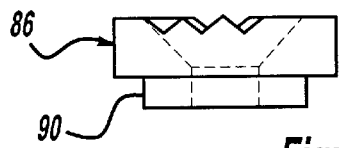
Figure 6A:
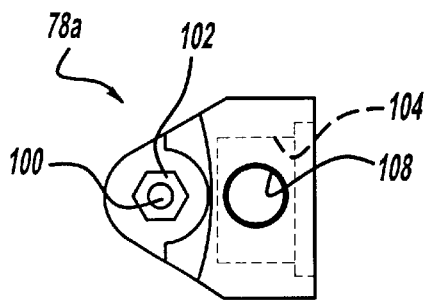
FIGS. 6A and 6B are illustrations of a rotational component shown in FIG. 2 according to the teachings of the preferred embodiment of the present invention.
Figure 6B:
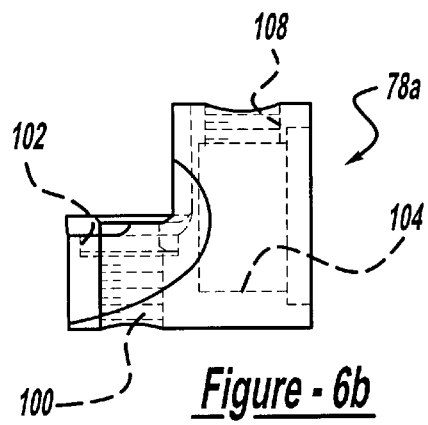

Referring to FIGS. 1A and 1B, an apparatus for external fixation of a hinged joint is generally identified with reference numeral 10. The apparatus or external fixator 10 is illustrated operatively associated with a human elbow joint 12. However, it will become apparent to those skilled in the art that the teachings of the present invention have applicability to other hinged joints.

Before addressing the construction and function of the apparatus 10, a brief understanding of the pertinent elbow anatomy is warranted. The elbow joint 12 is a hinge type of synovial joint formed by the distal end of the humerus and the proximal ends of the radius and ulna. The elbow is a uniaxial joint and its movements consist of flexion and extension. The trochlea and capitulum of the humerus articulate with the trochlear notch of the ulna and the head of the radius, respectively.

FIG. 1B shows in a simplified manner, the apparatus 10 interconnected to a first bone 14 on the proximal side of the elbow joint 12 and a second bone 18b on the distal side of the joint. In the exemplary arrangement illustrated, the first bone is the humerus 14 and the second bone is the ulna 16.

With continued reference to FIGS. 1A and 1B, the apparatus 10 is shown preferably connected to the humerus 14 through at least a first bone screw 18a and to the ulna 16 through at least a second bone screw 18b. By securing the humerus 14 and ulna 16 in this manner, the anatomical pivot axis of the elbow joint 12, which is located therebetween, may be stabilized. Again, while the apparatus 10 is specifically shown associated with an elbow joint 12, it is to be understood that the teachings of the present invention may be adapted for use with other hinged joints of the body.

With continued reference to FIGS. 1A and 1B and additional reference to FIGS. 2–10, the apparatus 10 is shown to generally comprise a central ring assembly 24, a first bone screw clamping assembly 26 and a second bone screw clamping assembly 28. The ring assembly or main body 24 is adjustably interconnected to both of the first and second bone screw clamping assemblies 26 and 28 to allow for adjustment of the bone screws 18 relative to the mechanical pivot axis. The first bone screw clamping assembly 26 is used to secure the first bone screw 18a to the apparatus 10 while permitting the first bone screw 18a to be axially displaced from the central ring assembly 24. The second bone screw clamping assembly 28 similarly is used to secure the second bone screw 18b to the apparatus 10 while permitting the second bone screw 18b to be axially displaced from the central ring assembly 24.

According to one particular aspect, the present invention relates to the construction and operation of the central ring assembly 24 and the adjustable interconnections between the central ring assembly 24 and the first and second clamping assembly 26 and 28. In this regard, it will be understood that the first and second bone screw clamping assemblies 26 and 28 may be of any suitable configuration for receiving the bone screws 18. For purposes of fully describing the exemplary embodiment illustrated throughout the drawings, the first and second clamping assembly 26 and 28, as well as the central ring assembly 24 and the interconnections between the central ring assembly 24 and the first and second bone screw clamping assembly 26 and 28, will be more fully discussed below.

The first bone screw clamping assembly 26 will be described in greater detail with reference to FIGS. 3A–3B. It is to be understood that while only the first bone screw clamp 26 is being described, the second bone screw clamp 28 will have a similar construction. The first bone screw clamping assembly 26 includes a base portion 30 and a cover portion 32. The base portion 30 preferably serves to receive two bone screws 18a in two of a plurality of grooves 34, while the cover portion 32 serves to secure the bone screws 18a within the grooves 34. The grooves 34 include two contact surfaces which are substantially planar so as to permit line contact of the bone screws 18 in two positions within the grooves 34. Since the first bone screw 18a also engages the cover portion 32 of the first bone screw clamping assembly 26, the bone screws 18 engage the first bone screw clamping assembly 26 in three positions (i.e., along the contact surfaces as well as on the cover portion 32). This provides line contact for the bone screw 18 which secures the bone screws 18 in a more effective manner than if the grooves 34 were cylindrical.

The base portion 32 of the bone screw clamping assembly 26 further includes a first aperture 36 and a second aperture 38. The first aperture 36 is used to receive a threaded member 40 which serves to secure a rail member 42 in a locked position as will be more fully discussed below. The second aperture 38 is used to receive a threaded member 44 which is able to secure a compression/distraction member (not shown) within a D-shaped central bore 46 of the bone screw clamping assembly 26. One suitable compression/distraction member is shown and described in U.S. Pat. No. 5,662,650.

The cover portion 32 of the first bone screw clamping 26 is secured to the base portion 30 by means of two screws 48. To accommodate these screws 48, the cover portion 32 of the bone screw clamping assembly 26 includes two apertures 50 (shown in phantom in FIGS. 3(A) and 3(B)) which mate with corresponding apertures 52 in the base portion 30 of the bone screw clamp 26. Accordingly, upon secured threaded engagement of the screws 48 within the apertures 50 and 52, the cover portion 32 of the bone screw clamp 26 may be secured to the base portion 30 of the bone screw clamp 26.

To provide means for laterally displacing the first bone screw clamp 26 with respect to the central body 24, the bone screw clamping assembly 26 further includes the rail member 42. The rail member 42, which is illustrated most clearly in FIGS. 4A–4C, includes a D-shaped extension 54 which is able to receive in the D-shaped bore 46 of the bone screw clamping assembly 26. Because of the cross-sectional shape of the D-shaped extension 54, the base portion 30 of the bone screw clamping assembly 26 is able to slide on the D-shaped extension 54 of the rail member 42, though the base portion 30 is unable to rotate with respect to the D-shaped extension 54.

The rail member 42 further includes a groove 56 which is disposed on the surface of the D-shaped extension 54. The location of the groove 56 is such as to permit the groove 56 to be located adjacent to the aperture 36 when the D-shaped extension 54 of the rail member 42 is inserted into the D-shaped bore 46 of the base portion 30. As will be apparent to those skilled in the art, the threaded member 40 can then be inserted into the aperture 36 of the base portion 30 of the bone screw clamping assembly 26 so as to securely engage the groove 56 of the D-shaped extension 54 thereby preventing axial movement of the base portion 30 with respect to the rail member 42. In the preferred embodiment, the groove 56 includes graduated markings (not specifically shown) indicating the relative amount of longitudinal displacement of the bone screw clamping assembly 26 relative to the central body 24.

To provide means for displacing the second bone screw clamp 28 with respect to the central body 24, the second bone screw clamp 28 similarly includes a second rail member 42b. As with the first rail member 42a, the second rail member 42b has a D-shaped extension 54 which is able to receive the D-shaped bore 46 of the second bone screw clamp 28. Again, because of the cross-sectional shape of the D-shaped extension 54, the base portion 30 of the second bone screw clamp 28 is able to slide on the D-shaped extension 54 of the second rail member 42b, though the base portion 30 is unable to rotate with respect to the D-shaped extension 54.

Figure 10:
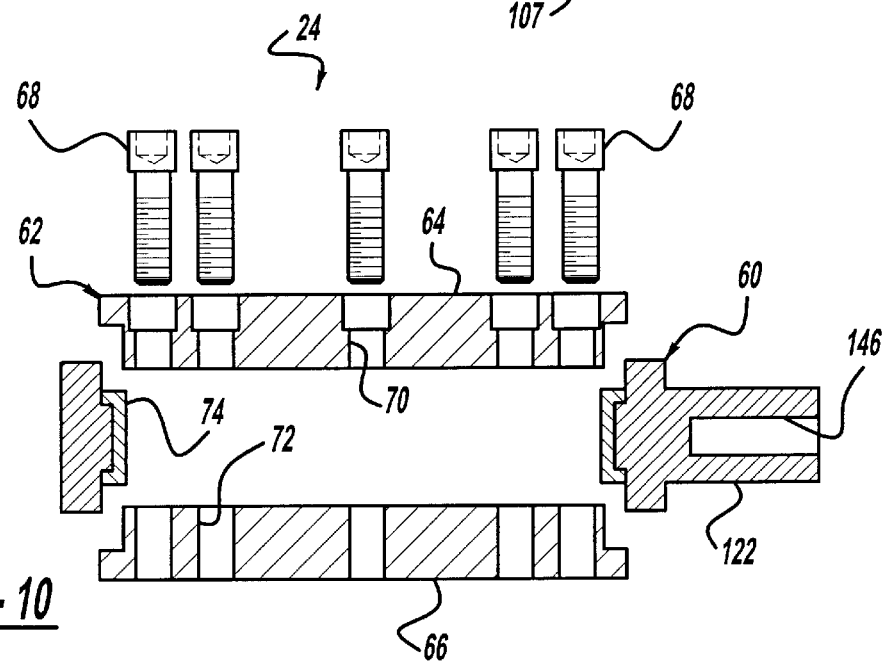
FIG. 10 is an exploded view of the ring assembly shown in FIG. 2 according to the teachings of the preferred embodiment of the present invention, illustrated in cross section.

With specific reference to FIGS. 2 and 10, the central ring assembly 24 will now be described in greater detail. The ring assembly 24 is shown to generally include an outer ring member 60 and an inner ring member 62. The outer and inner ring members 60 and 62 are coincentrially arranged and adapted to rotate relative to each other about a common centerpoint. In the embodiment illustrated, the inner ring member 62 includes first and second halves 64 and 66. The first and second halves 64 and 66 are joined by a plurality of threaded fasteners 68. To accommodate these fasteners 68, the first half 64 includes apertures 70 which mate with corresponding apertures 72 in the second half 66. Upon secured threaded engagement of the threaded fastener 68 with the aperture 72 in the second half 66, the first and second halves 64 and 66 are interconnected and the outer ring member 60 is rotatably captured therebetween. In the embodiment illustrated, a suitable bearing 74 is provided between adjacent surfaces of the inner and outer members 60 and 62.

To provide means for adjustably interconnecting the central ring assembly 24 with the first clamping assembly 26, the apparatus 10 of the present invention is shown to include a first rotational component 78a, a first connection member 80a, and an outer ring attachment component 82. To provide means for adjustably interconnecting the central ring assembly 24 with the second clamping assembly 28, the apparatus 10 is shown to generally include a second rotational component 78b, a second connection member 80b and an inner ring attachment component 84. It is to be understood that while only the first rotational component 78a and the first connection member 80a are being described, the second rotational component 78b and the second connection member 80b, respectively, have a similar construction.

A pair of grooved locking washers 86 is disposed between the first rail member 42a and the first connection member 80a, as well as between the second rail member 42b and the second connection member 80b. In particular, the first rail member 42a has an aperture 87 with a hex-shaped recess 88 for receiving a base portion 90 of the washer 86, while the second rail member 42b also has an aperture with a hex-shaped recess for receiving the base portion 90 of the washer 86.

In a similar fashion, the first connection member 80a also includes an aperture 92 with a hex-shaped recess 94 for receiving the base portion 90 of the washer 86, while the second connection member 80b also has an aperture with a hex-shaped recess for engaging the base portion 90 of the washer 86. Because the groove surfaces of adjacent washer 86 engage each other, the first rail member 42a is secured to the first connection member 80a upon secured threaded engagement of a screw 96, while the second rail member 42b is secured to the second connection member 80b upon threaded engagement of the screw 96. The first and second connection members 80a and 80b permit approximately 60° of relative rotation between the first and second bone screw clamps 26 and 28, respectively, with respect to the central body 24.

The first and second connection members 80a and 80b are also secured to the first rotational component and second rotational component 78a and 78b, respectively, each by a pair of locking washers 86. In this regard, first connection member 80a includes an aperture with a hex-shaped recess for receiving the base portion 90 of the washer 86, while the second connection member 80b similarly has an aperture with a hex-shaped recess for receiving the base portion 90 of the washer 86. In a similar fashion, the first rotational component 78a also has an aperture 100 with a hex-shaped recess 102 for receiving the base portion 90 of the washer 86, while the second rotational component also has an aperture with a hex-shaped recess for receiving the base portion 90 of the washer 86. The grooves in the washers 86 allow more secure attachment between the first and second connection members 80a and 80b and the first and second rotational components 78a and 78b, respectively, when they are secured by the bolts 96.

The first rotational component 78a defines a bore 104 which is able to receive a male extension portion 106 of the outer ring connection member 82 and includes an aperture 108 which is able to receive a threaded member 110 (shown in FIG. 2). The male extension 106 includes a reduced diameter portion 107 which is able to be located proximate to the aperture 108 in the first rotational component 78a. When the threaded member 110 is inserted through the aperture 108 in the first rotational component 78a and is allowed to engage the male extension portion 106 of the outer ring connection member 82, the first rotational component 78a and the outer ring connection member 82 are securely locked so as to prohibit relative rotational movement.

Similarly, the second rotational component 78b defines a bore which is able to receive a male extension portion 112 of the inner ring connection member 84 and includes an aperture which is able to receive a threaded member 114. The male extension portion 112 includes a reduced diameter portion 116 which is able to be located proximately to the aperture in the second rotational component 78b. When the threaded member 114 is inserted through the aperture in the second rotational component 78b and is allowed to engage the male extension portion 112, thereby relative rotation therebetween is prevent.

Figure 9:
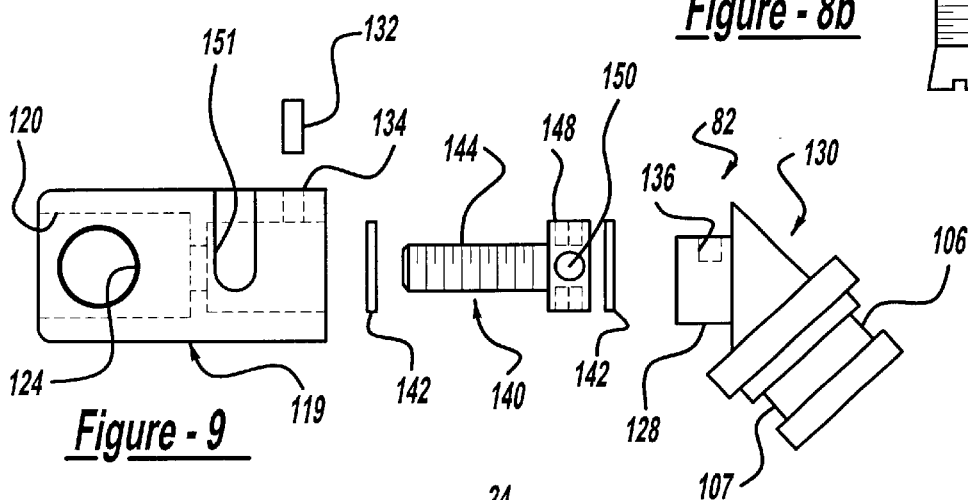
FIG. 9 is an exploded view of an outer ring attachment component shown in FIG. 2 according to the teachings of the preferred embodiment of the present invention.

The outer ring attachment component 84 is shown most clearly in FIG. 9 to include a connector member 119 which defines an internal bore 120. A first end of the bore 120 is adapted to receive a male extension 122 integrally formed with the outer ring member 60. The connector member 119 further includes a threaded aperture 124 which intersects the bore 120 and is adapted to receive a threaded fastener 126. The threaded fastener 126 operates when tightened to interconnect the outer ring member 60 and the outer ring attachment component 82 and prevent relative movement therebetween.

A second end of the bore 120 is adapted to receive a male extension 128 carried by an angled member 130 which also carries the male extension portion 106. The angled member 130 is securely attached to the connector member 119 through a pin 132 which is adapted to pass through an aperture 134 which intersects the bore 120 and engages a corresponding aperture 136 provided in the male extension 128. In the embodiment illustrated, the angle between the male extension 128 and the male extension portion 106 of the angled member 130 is approximately 45°.

To provide means for translating the outer ring attachment component 82 relative to the ring assembly 24, the outer ring attachment component 82 includes a threaded member 140 disposed within the bore 120. The threaded member 140 is rotatably supported by a pair of suitable bearings 142 and includes an externally threaded shaft 144 adapted to engage an internally threaded bore 146 provided in the male extension portion 122 of the outer ring member 60. The threaded fastener 140 further includes a head 148 formed to include a plurality of apertures 150. The apertures 150 are accessible through an elongated slot 151 provided in the connector member 119. In use, translation of the connector member 119 is accomplished by rotating the threaded fastener 140 with an alien wrench or similar tool adapted to engage one of the apertures 150 provided in the head 148. The angled member 130 allows the apparatus 10 to distract the humerus perpendicular to the proximal end of the ulna (i.e., perpendicular to the tips of the olecranon and coronoid processes of the ulna). The direction of distraction is identified in FIG. 1A by arrow A.

Figure 8A:
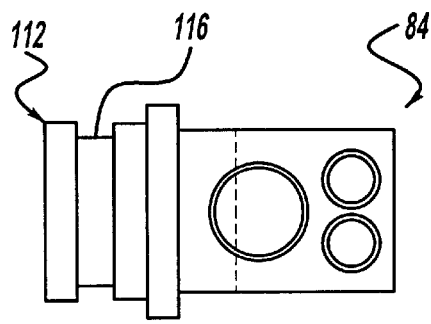
FIGS. 8A and 8B are illustrations of an inner ring attachment component shown in FIG. 2 according to the teachings of the preferred embodiment of the present invention.
Figure 8B:
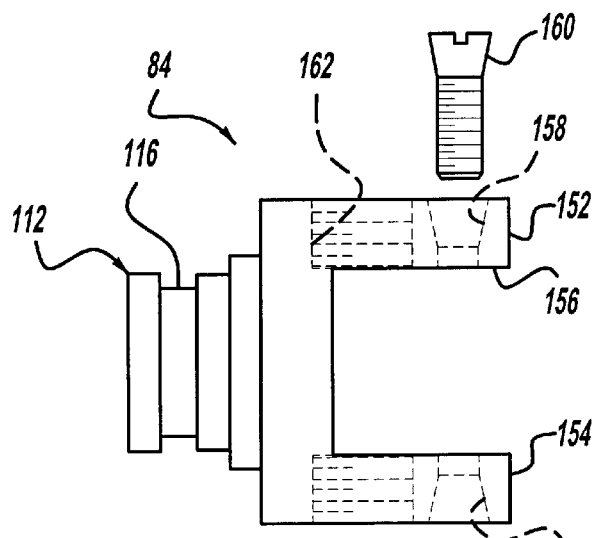

Turning to FIGS. 8A and 8B, the inner ring attachment component 84 is shown to include first and second spaced apart flanges 152 and 154 which define a recess 156 therebetween adapted to rotatably accommodate the ring assembly 24. Both of the flanges 152 and 154 include a pair of apertures 158 adapted to receive a threaded fastener 160. The threaded fastener 160 is adapted to pass through the aperture and lockingly engage corresponding apertures (not specifically shown) provided in the inner ring member 62 of the ring assembly 24. The inner ring connection component 84 allows the second bone clamping assembly 28 to be interconnected to the inner ring member 62 while allowing the inner ring member 62 to rotate relative to the outer ring member 60. In this manner, the humerus 14 and ulna 16 are permitted to rotate relative to one another about the anatomical pivot axis of the elbow 12.

The first flange 152 includes a second threaded aperture 162. The second threaded aperture 162 is adapted to receive a threaded fastener 164 (shown in FIG. 2). Upon tightening, the threaded fastener 164 is adapted to engage the outer ring member 60 and selectively prevent relative rotation of the inner and outer ring members 60 and 62.

Figure 11A:
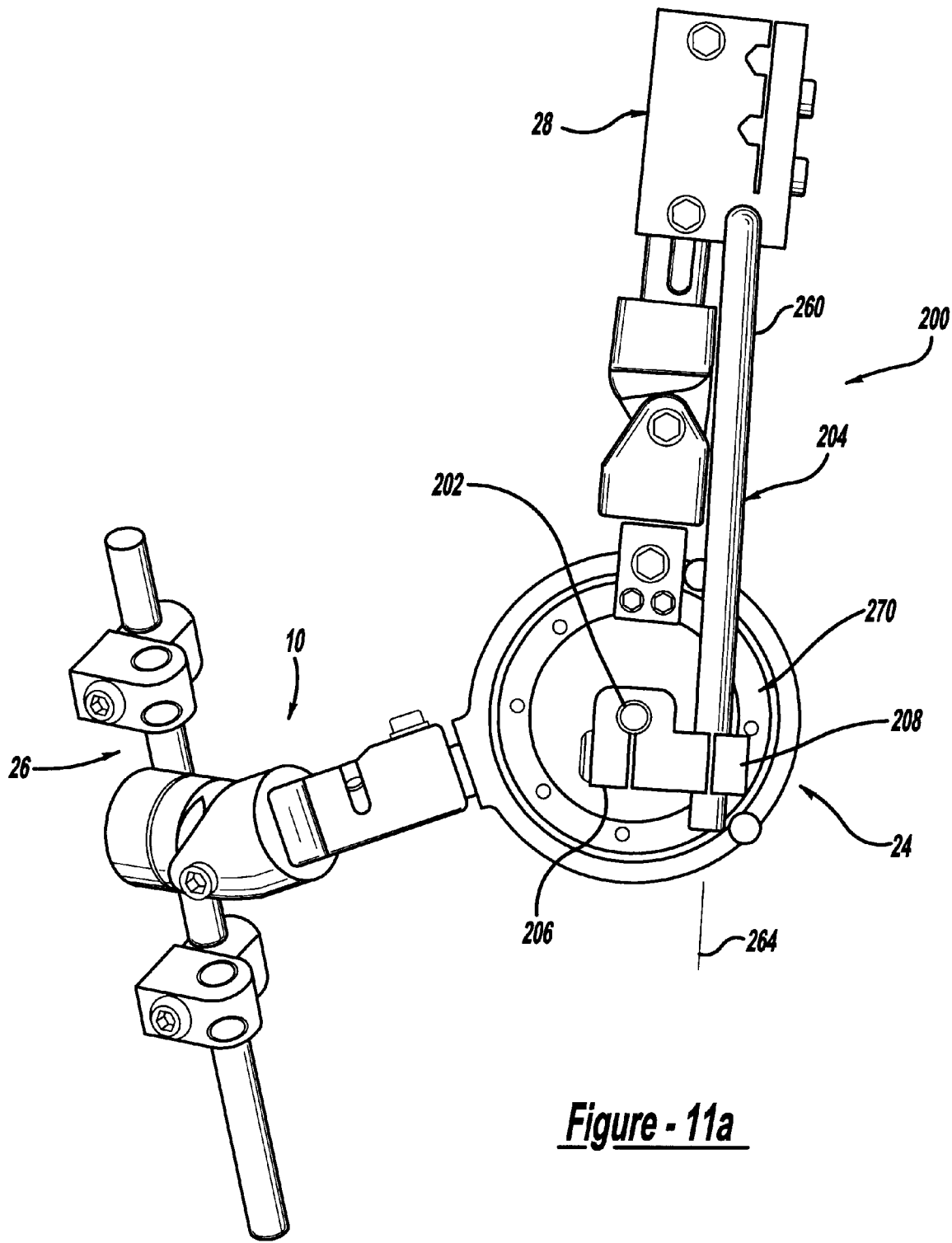
FIGS. 11A and 11B are views of an apparatus for aligning the mechanical pivot axis of an external fixator with an anatomical pivot axis, the apparatus shown operatively with the external fixator.
Figure 11B:
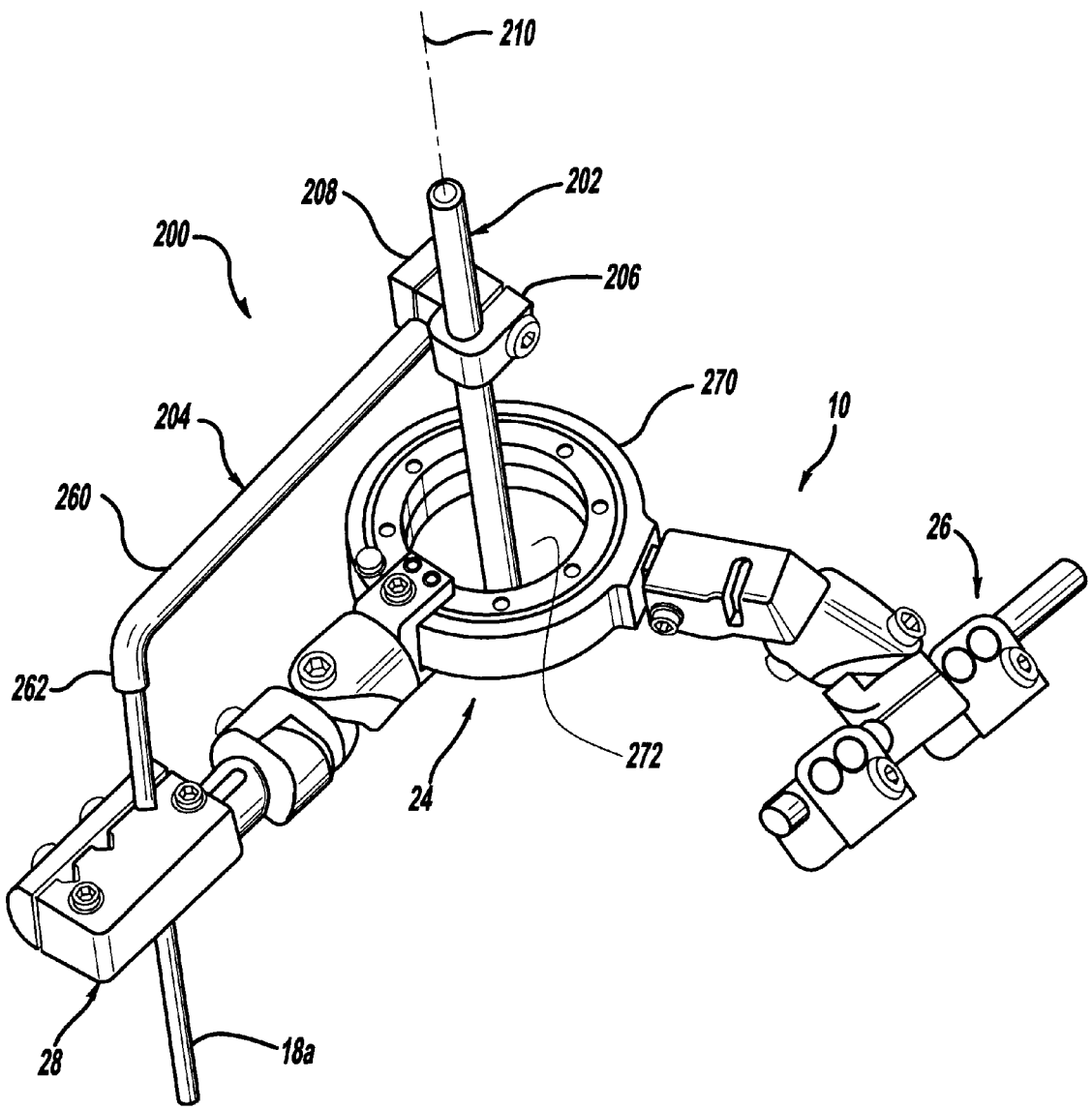

With reference to FIGS. 11A and 11B, an apparatus for aligning an external fixator mechanical pivot axis and an anatomical pivot axis of a hinged joint constructed in accordance with the teachings of the present invention is illustrated and generally identified at reference number 200. For purpose of illustration, the apparatus for axes alignment 200 is shown operatively assembled with the external fixator 10 of FIGS. 1–10. The manner of attachment to the radial bone screws 186 (shown in FIG. 1B) has been modified slightly from that shown in FIGS. 1–10. An alternative construct of an apparatus for axes alignment 200' is illustrated in FIG. 13 and will be described below. It will be understood that the apparatus for axes alignment 200 or 200' may be used with constructs of the external fixator 10 other than that shown in the drawings, as well as other external fixation devices including those for other hinged joints.

The apparatus for axes alignment 200 of the present invention is illustrated to generally include an alignment member 202 and a connecting member or linkage member 204. The apparatus 200 further includes suitable clamps 206 and 208 for adjustably attaching the alignment member 202 to the connecting member 204.

The alignment member 202 defines an alignment axis 210 adapted to be aligned with the anatomical pivot axis of a hinged joint. In the exemplary embodiment, the alignment member 202 is illustrated as a hollow tube constructed of metal or other radiographic material. Alternatively, it will be understood that a solid rod may be used within the scope of the present invention. The alignment member 202 is adjustably secured to the connecting member 204 through a first clamp 206 and a second clamp 208.

Figure 13A:
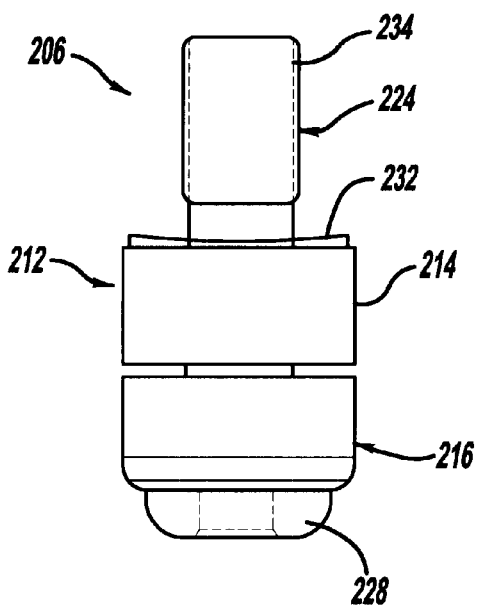
FIGS. 13A and 13B are views of a first clamp of the apparatus for aligning according to the teachings of the preferred embodiment of the present invention.
Figure 13B:
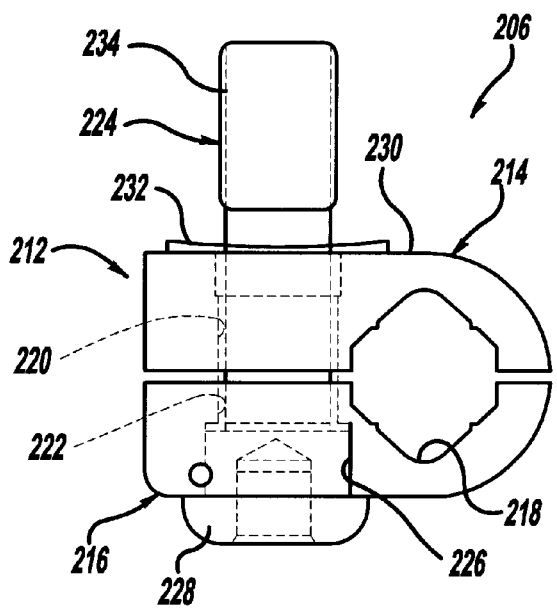

With reference to FIGS. 13A and 13B, the first clamp or base clamp assembly 206 of the apparatus 200 of the present invention is further illustrated. The base clamp 206 includes a clamp portion 212 having first and second halves 214 and 216 which cooperate to define an aperture 218 for receiving the alignment member 202. The first and second halves 214 and 216 include aligning apertures 220 and 222, respectively, for receiving a locking bolt or fastener 224. The aperture 222 of the second half 216 includes a counterbored portion 226 for receiving a portion of a head 228 of the fastener 224. An outer surface 230 of the first half 214 is formed to include a serrated portion 232 having a plurality of serrations radially extending from the opening of the aperture 220. An end 234 of the fastener 224 opposite the head 228 is externally threaded.

Figure 14A:
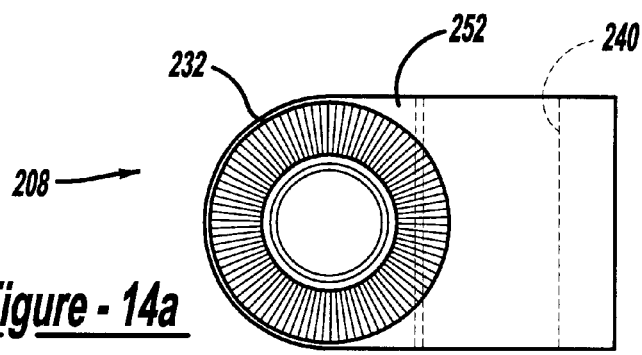
FIGS. 14A through 14C are views of a second clamp of the apparatus for aligning according to the teachings of the preferred embodiment of the present invention.
Figure 14B:
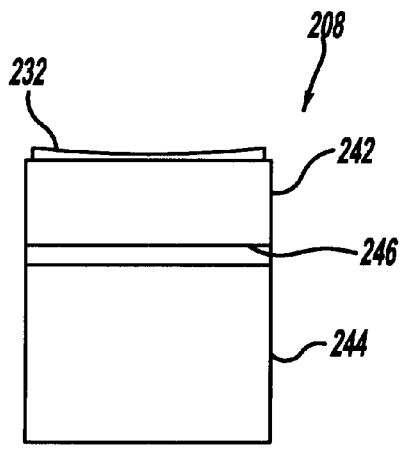
Figure 14C:
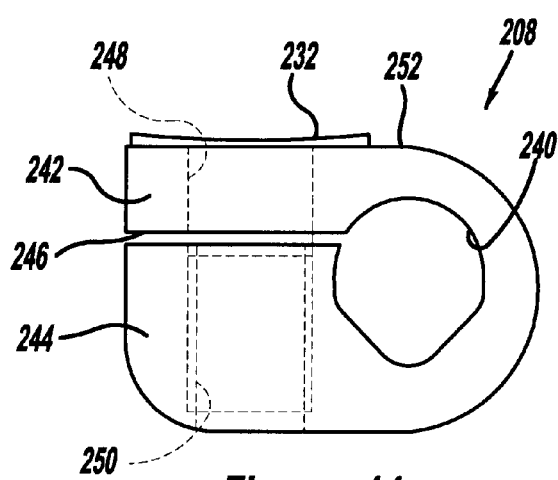

With reference to FIGS. 14A through 14C, the second clamp 208 of the apparatus 200 of the present invention is particularly illustrated. The second clamp 208 is generally C-shaped to define an aperture 240 and includes first and second ends 242 and 244 which are spaced apart by an opening 246. The first and second ends 242 and 244 include aligning apertures 248 and 250, respectively, for receiving the fastener 224. The aperture 250 of the second end 244 is internally threaded. An outer surface 252 of the first end 242 is formed to include a serrated portion 232.

The second clamp 208 is attached to the base clamp assembly 206 through engagement of the fastener 224 with the apertures 248 and 250. In such engagement, the serrated portions 72 of the components are interlocked thereby preventing relative rotation. When the fastener 228 is rotated to draw the cooperating component against the first half 216, the first and second halves 214 and 216 of the clamp portion 212 are drawn together to thereby securely clamp the alignment member 202 within the aperture 218. Tightening of the fastener 224 draws the ends 242 and 244 of the second clamp body 208 toward one another. As a result, the connecting member 204 positioned within the aperture 240 is secured relative to the alignment member 202.

In the embodiment of FIGS. 11A and 11B, the connecting member 204 of the apparatus 200 is generally L-shaped having a first leg 260 and a second leg 262. The first leg 260 defines a longitudinal axis 264. The second leg 262 receives an upper end of one of the humeral bone screws 18a. While not particularly illustrated, it will be understood that the humeral bone screw 18a and the second leg 262 of the connecting member 260 can be similarly configured to have cooperating and non-cylindrical shapes to prevent relative rotation between the connecting member 204 and the humeral bone screw 18b.

Figure 12:
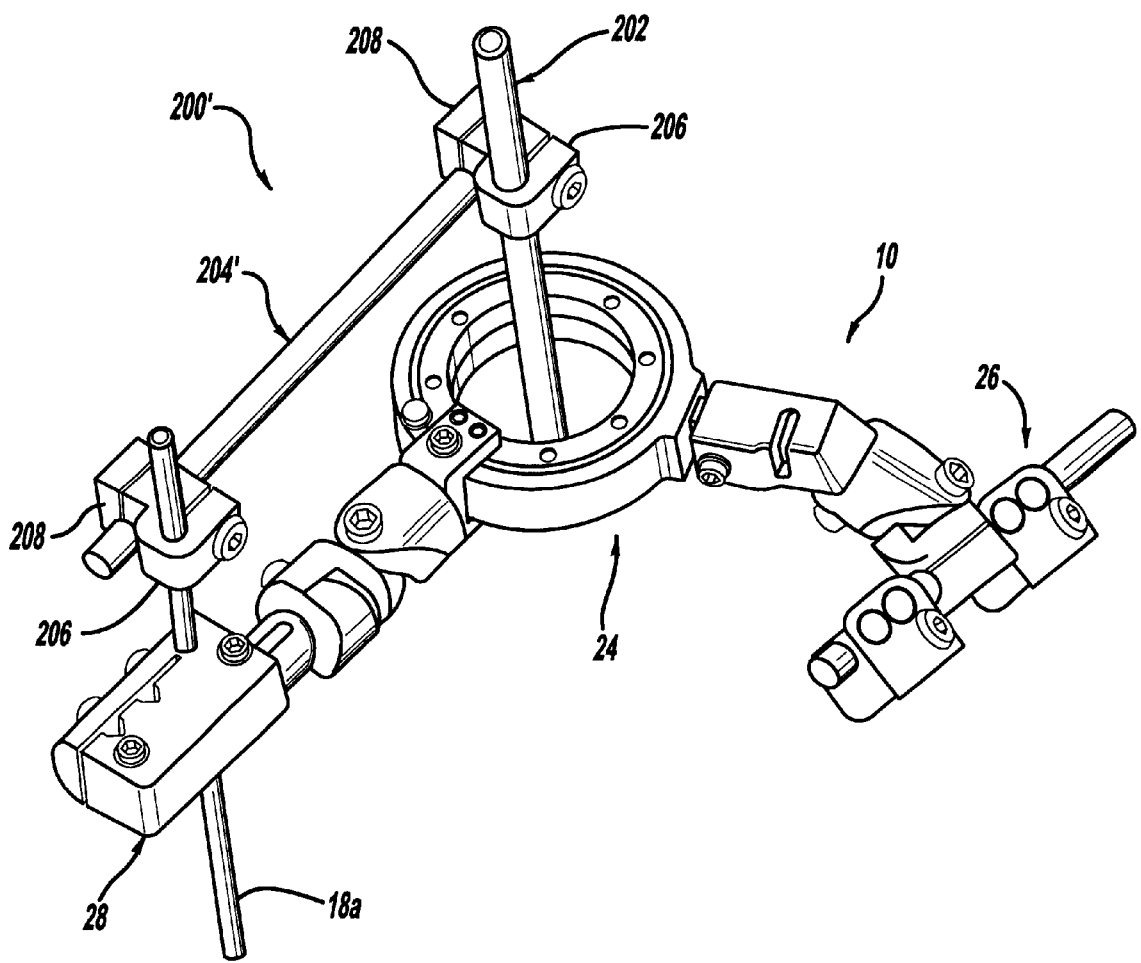
FIG. 12 is a view similar to FIG. 11B illustrating an alternative manner of interconnecting the alignment member to the bone screw clamping assembly.

In the construct of FIG. 12, the apparatus 200' includes a connecting member 204' in the shape of a cylindrical rod. In this embodiment, the connecting member 204 is adjustably secured to one of the humeral bone screws 18a with first and second clamps 206 and 208 substantially identical to those described above.

In the embodiments illustrated, the axis 264 of the connecting member 204 is substantially perpendicular to the longitudinal axis 210 of the alignment member 202. However, this particular orientation is not required and relative adjustment may be desirable. To this end, the connecting member 204 or 204' is rotatable relative to the alignment member 202 about an axis substantially perpendicular to the longitudinal axis 210. Such relative rotation is achieved through relative rotation between the first and second clamps 206 and 208 at the joint defined between the cooperating serrations 232. In addition, the alignment member 202 is adjustable relative to the connecting member 204 or 204' along the longitudinal axis 210 through movement of the alignment member 202 through the aperture 218. Similarly, the alignment member 202 is adjusted relative to the connecting member 204 in a direction perpendicular to the longitudinal axis 210 by passing the connecting member 204 or 204' through the aperture 240. In the construct of FIG. 12, similar adjustments can be made between the humeral bone screw 18a and the connecting member 204'.

The present invention further includes a template 270 to assist with alignment of the alignment member 202 relative to the mechanical pivot axis of the external fixator 10. The template 270 is shown with the construct of FIGS. 11A and 11B. However, it will be appreciated that the template can also be used with the construct of FIG. 12.

The template 270 is secured to the central body 24 of the external fixator 10 and includes a centrally located aperture 272. The aperture 272 is aligned with the mechanical pivot axis of the external fixator 10. The aperture 272 is sized to receive the alignment member 202. In the preferred embodiment, the template 270 is constructed of a radiotransparent material.

The method of the present invention will be detailed with particular reference to the construct of FIG. 12. The method of the present invention particularly relates to a method of aligning a mechanical pivot axis of an external fixator 10 with an anatomical pivot axis of hinged joint. In a first general step, an external fixator is pivoted having first and second bone screw clamping assemblies 26 and 28 connected by a central body 24. The central body 24 defines the mechanical pivot axis.

In a second general step of the method of the present invention, a bone screw 18a is secured to the humerus 14.

In a third general step of the method of the present invention, the longitudinal axis 210 of the alignment member 202 is aligned with the anatomical pivot axis. In one preferred application, the anatomical pivot axis is radiographically identified with a fluoroscopic beam.

In the fourth general step of the method of the present invention, the alignment member 202 is interconnected to the bone screw 18a. The alignment member 202 is preferably connected to the bone screw 18a through a connecting member 204 or 204'. First and second clamps 206 and 208 are used to adjustably connect alignment member 202 with connecting member 204'. Similarly, first and second clamps 206 and 208 are used to connect first bone screw 18a with connecting member 204'. At this point, a fixed relative position is established between the anatomical pivot axis and the bone screw 18a.

In a fifth general step of the method of the present invention, the bone screw clamp assembly 28 is secured to the bone 14 through the first bone screw 18a.

In a sixth general step of the method of the present invention, the longitudinal axis 210 of the alignment member 202 is aligned with the mechanical pivot axis of the external fixator 10. In one application, the template 270 is secured to the central body 24 of the external fixator and the alignment member 202 passes through the central aperture 272 of the template 270. Alternatively, the alignment member 202 can be visually aligned with the mechanical axis of the external fixator 10.

At this point, the humeral side of the external fixator 10 is locked up and the relative positions between the clamp assembly 28 and the central body 24 of the external fixator 10 are arrested. If the surgeon so desires, the apparatus for axes alignment 200 can now be removed from the external fixator 10 through loosening of the first and second clamps 206 and 208 connecting the connecting member 204 and the bone screw 18a. Attachment of the external fixator 10 is now completed by securing the bone screw clamp assembly 26 to the radius 16 through radial bone screws 18b.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention.

What is claimed is:

1. An apparatus for aligning a mechanical pivot axis of an external fixator with an anatomical pivot axis of a hinged joint, the hinged joint having first and second bones on opposite sides of the anatomical pivot axis, the external fixator having a central body connecting a first bone screw clamping assembly and a second bone screw clamping assembly, the central body including the mechanical pivot axis, the apparatus for aligning comprising:

an alignment member having a longitudinal axis for alignment with the anatomical pivot axis; and a connecting member adjustably secured to the alignment member and adjustably secured to the first bone screw clamping assembly.

2. The apparatus for aligning a mechanical pivot axis of an external fixator with an anatomical pivot axis of a hinged joint of claim 1, wherein the connecting member is rotatable relative the alignment member about an axis substantially perpendicular to the longitudinal axis.

3. The apparatus for aligning a mechanical pivot axis of an external fixator with an anatomical pivot axis of a hinged joint of claim 1, wherein the alignment member is adjustable relative the connecting member along the longitudinal axis.

4. The apparatus for aligning a mechanical pivot axis of an external fixator with an anatomical pivot axis of a hinged joint of claim 1, wherein the connecting member is generally L-shaped.

5. The apparatus for aligning a mechanical pivot axis of an external fixator with an anatomical pivot axis of a hinged joint of claim 3, wherein the alignment member is adjustable relative to the connecting member in a direction perpendicular to the longitudinal axis.

6. The apparatus for aligning a mechanical pivot axis of an external fixator with an anatomical pivot axis of a hinged joint of claim 1, wherein an axis of the connecting member is substantially perpendicular to the longitudinal axis.

7. The apparatus for aligning a mechanical pivot axis of an external fixator with an anatomical pivot axis of a hinged joint of claim 1, wherein the first bone screw clamp assembly includes a first bone screw for attachment to the first bone and wherein the connecting member is adjustably secured to the first bone screw.

8. An arrangement for external fixation of a hinged joint having an anatomical pivot axis interdisposed between first and second skeletal elements, the first and second skeletal elements located on opposite sides of the hinged joint, respectively, the arrangement comprising:

a central body defining a mechanical pivot axis;

first bone screw clamping assembly having a said first bone screw adapted to be connected to the first skeletal element, the first bone screw clamping assembly interconnected to the central body;

a second bone screw clamping assembly having a second bone screw adapted to be connected to the second skeletal element, the second bone screw clamping assembly interconnected to the central body; and an apparatus for aligning the mechanical pivot axis with the anatomical pivot axis, the apparatus including:

an alignment member having a longitudinal axis for alignment with the anatomical pivot axis; and a connecting member adjustably secured to the alignment member and adjustably secured to the first bone screw clamping assembly.

9. The arrangement for external fixation of a hinged joint of claim 8, wherein the connecting member is rotatable relative the alignment member about an axis substantially perpendicular to the longitudinal axis.

10. The arrangement for external fixation of a hinged joint of claim 8, wherein the alignment member is adjustable relative to the connecting member along the longitudinal axis.

11. The arrangement for external fixation of a hinged joint of claim 8, wherein the connecting member is generally L-shaped.

12. The arrangement for external fixation of a hinged joint of claim 10, wherein the alignment member is adjustable relative to the connecting member in a direction perpendicular to the longitudinal axis.

13. The arrangement for external fixation of a hinged joint of claim 8, wherein an axis of the connecting member is substantially perpendicular to the longitudinal axis.

14. The arrangement for external fixation of a hinged joint of claim 8, wherein the connecting member is adjustably secured to the first bone screw.

15. A method of aligning a mechanical pivot axis of an external fixator with an anatomical pivot axis of a hinged joint, the hinged joint having first and second bones on opposite sides of the anatomical pivot axis, the method of comprising the steps of:

providing an external fixator having first and second bone screw clamping assemblies connected by a central body, the central body having a mechanical pivot axis;

securing a first bone screw to the first bone;

aligning a longitudinal axis of an alignment member with the anatomical pivot axis;

interconnecting the alignment member with the first bone screw;

securing the first bone screw clamp assembly to the first bone through at least one bone screw; and aligning the longitudinal axis of the alignment member with the mechanical pivot axis.

16. The method of aligning a mechanical axis of an external fixator with an anatomical axis of a hinged joint of claim 15, wherein the step of aligning the longitudinal axis of the alignment member with the anatomical pivot axis includes the step of radiographically identifying the anatomical pivot axis.

17. A method of aligning a mechanical axis of an external fixator with an anatomical axis of a hinged joint of claim 16, wherein the step of aligning the longitudinal axis of the alignment member with the anatomical pivot axis further includes the step of radiographically aligning the longitudinal axis with the anatomical pivot axis.

18. A method of aligning a mechanical axis of an external fixator with an anatomical axis of a hinged joint of claim 15, wherein the alignment member is a hollow tube.

19. A method of aligning a mechanical axis of an external fixator with an anatomical axis of a hinged joint of claim 15, wherein the step of aligning the longitudinal axis of the alignment member with the mechanical pivot axis includes the step of visually aligning the longitudinal axis with the mechanical pivot axis.

20. A method of aligning a mechanical axis of an external fixator with an anatomical axis of a hinged joint of claim 15, wherein the step of aligning the longitudinal axis of the alignment member with the mechanical pivot includes the steps of:

securing a template to the external fixator, the template having an aperture aligned with the mechanical pivot axis; and passing the alignment member through the aperture in the template.

* * * * *